(12) United States Patent
Lee et al.

(10) Patent No.: US 11,660,171 B2
(45) Date of Patent: May 30, 2023

(54) SYSTEM, METHOD AND COMPUTER PROGRAM FOR PRODUCING IMPLANT PLACING GUIDE

(71) Applicant: IMSOL CORP., Gyeonggi-do (KR)

(72) Inventors: Ji Hae Lee, Gyeonggi-do (KR); Da Som Heo, Gyeonggi-do (KR)

(73) Assignee: IMSOL CORP.

(*) Notice: Subject to any disclaimer, the term of this patent is extended or adjusted under 35 U.S.C. 154(b) by 739 days.

(21) Appl. No.: 16/657,805

(22) Filed: Oct. 18, 2019

(65) Prior Publication Data

US 2021/0113310 A1    Apr. 22, 2021

(51) Int. Cl.
*G06T 7/73* (2017.01)
*A61C 13/00* (2006.01)
(Continued)

(52) U.S. Cl.
CPC .......... *A61C 13/0004* (2013.01); *A61B 6/032* (2013.01); *A61C 9/0006* (2013.01);
(Continued)

(58) Field of Classification Search
CPC ..... A61C 13/0004; A61C 9/0053; G06T 7/73; G16H 30/20; A61B 6/032; A61B 9/0006; G06Q 20/28
See application file for complete search history.

(56) References Cited

U.S. PATENT DOCUMENTS

| | | | | |
|---|---|---|---|---|
| 2011/0123946 A1* | 5/2011 | Bulloch | ................. | A61C 1/084 433/173 |
| 2015/0265372 A1* | 9/2015 | Kim | ......................... | G06T 7/13 433/214 |

(Continued)

FOREIGN PATENT DOCUMENTS

| | | |
|---|---|---|
| KR | 10-2010-0117385 | 11/2010 |
| KR | 10-1659323 | 9/2016 |

(Continued)

OTHER PUBLICATIONS

International Search Report for PCT/KR2019/012528, dated Jun. 23, 2020, including English translation, 5 pages.

*Primary Examiner* — Edward Park

(74) *Attorney, Agent, or Firm* — Adsero IP

(57) ABSTRACT

According to the invention, there are provided a system, a method and a computer program for producing an implant placing guide. According to the invention, the system for producing an implant placing guide, includes: a dental-clinic terminal that transmits, to a managing server, a three-dimensional intraoral image acquired by a CT scan in a state where a guide tray filled with an impression material is inserted into an oral cavity of a patient and that receives an implant-placing-guide processing file from the managing server; a managing server that transmits a plan request signal to one or more preregistered planner terminals when receiving the three-dimensional image from the dental-clinic terminal and that generates an implant-placing-guide processing file by using implant planning information when receiving the implant planning information from a planner terminal that accepts the plan request signal; and a planner terminal that transmits, to the managing server, a signal of whether or not the plan request signal is accepted when the plan request signal is received from the managing server and that receives and transmits implant planning information corresponding to the three-dimensional image to the managing server when receiving the three-dimensional image from the managing server. The guide tray has one or more markers which are used for matching an image of the guide tray and the three-dimensional image and has an impression of a teeth shape of the patient. The implant planning information includes positional information of a guide hole which is formed at the guide tray. According to the invention, a time for producing an implant placing guide is significantly shortened, and thus convenience of a patient remarkably improves.

18 Claims, 10 Drawing Sheets

(51) Int. Cl.
*A61C 9/00* (2006.01)
*A61B 6/03* (2006.01)
*G06Q 20/28* (2012.01)
*G16H 30/20* (2018.01)

(52) U.S. Cl.
CPC ........... *A61C 9/0053* (2013.01); *G06Q 20/28* (2013.01); *G06T 7/73* (2017.01); *G16H 30/20* (2018.01); *G06T 2207/10081* (2013.01); *G06T 2207/30036* (2013.01); *G06T 2207/30052* (2013.01); *G06T 2207/30204* (2013.01)

(56) References Cited

U.S. PATENT DOCUMENTS

2016/0157967 A1\* 6/2016 Kim .................. A61C 8/005
433/201.1
2021/0113310 A1\* 4/2021 Lee .................... A61C 9/0006

FOREIGN PATENT DOCUMENTS

| KR | 10-1666982 B1 | 10/2016 |
| KR | 10-1918936 B1 | 11/2018 |
| KR | 10-2019-0122586 A | 10/2019 |
| KR | 10-2019-0046118 | 1/2020 |
| KR | 10-2019-0046123 | 1/2020 |
| KR | 10-2019-0046128 | 1/2020 |
| WO | 2015/154125 | 10/2015 |

\* cited by examiner

SYSTEM, METHOD AND COMPUTER PROGRAM FOR PRODUCING IMPLANT PLACING GUIDE

BACKGROUND OF THE INVENTION

Field of the Invention

The present invention relates to a system, a method and a computer program for producing an implant placing guide, more specifically, to a system, a method and a computer program for producing an implant fixture placing guide by using a known guide tray.

Description of the Related Art

A dental implant operation includes work for placing an implant fixture in an alveolar bone, and a guide tool which is often referred to as a guide stent or a surgical guide is widely used to appropriately place the implant fixture in the alveolar bone.

Currently, a guide stent used in an operative site is manufactured by a method similar to a method disclosed in Korean Patent No. 10-1473192 (Prior Literature 1, Title of the Invention: METHOD OF MANUFACTURING GUIDE STENT FOR DENTAL IMPLANT, Publication date: Dec. 16, 2014), Korean Patent No. 10-1554157 (Prior Literature 2, Title of the Invention: REFERENCE MARKER FOR ATTACHING INTRAORAL AND MANUFACTURING METHOD FOR GUIDE STENT OF DENTAL IMPLANT OPERATION USING THE SAME, Publication date: Sep. 21, 2015), and the like.

FIG. 1 in this specification illustrates [FIG. 1] in Prior Literature 2 showing a manufacturing method for a guide stent, and the manufacturing method for the guide stent in the related art is briefly described as follows, with reference to FIG. 1. First, in a dental clinic, a surgeon acquires a three-dimensional image of an oral cavity (intraoral periodontium) by a CT scan on a patient and acquires a three-dimensional external-shape image corresponding to the three-dimensional image by an oral scan (s1). The oral scan is performed by the surgeon by inserting a scanner in the oral cavity of the patient. As the scanning is performed along the oral cavity, a problem of image distortion often occurs; however, the oral scan needs to be performed to check a shape of a gum or a crown of a tooth of the patient because only a hard tissue is checked by the CT scan.

Image matching of the obtained three-dimensional image of the oral cavity and the obtained external-shape image of the patient is performed based on a characteristic of a tooth or a marker contained in the images, and a three-dimensional operative guide image is generated through the image matching (s2). The surgeon plans an implant operation using the three-dimensional operative guide image (s3) and manufactures a stent body having a guide hole in accordance with the operative guide image (s4).

In general, the first step (s1) to the last step (s4) are executed for a time of about two to three days. This is because the steps are not all executed by one main performer. In particular, a guide stent is manufactured by a guide stent manufacturer possessing high-precision processing equipment, rather than an implant surgeon (dentist), and thus a long time has to be taken from manufacturing a guide stent by the guide stent manufacturer after a three-dimensional operative guide image is obtained or an implant operating plan is established, to a delivery of the guide stent to the surgeon. Even though a dental clinic has equipment such as a 3D printer, it takes quite a long time to perform 3D printing, and thus a patient endured inconvenience of costs and time.

Besides, an external-shape image acquired by an oral scan has unavoidable distortion, and thus a problem arises in that a guide stent made through image matching will not accurately match an oral structure of a patient in many cases.

SUMMARY OF THE INVENTION

The invention is made to solve the above-described problem, and an object thereof is to significantly shorten a time for producing a guide stent and thus to remarkably improve convenience of a patient.

In addition, another object of the invention is to provide a system for producing an implant placing guide using a known tray, and thereby, to easily generate a profit by every performer participated in the producing of the implant placing guide and to achieve fair profit distribution.

In addition, still another object of the invention is to provide a system, a method, and a computer program for producing a guide, by which it is possible to easily plan and correct an implant placing guide.

In addition, still another object of the invention is to provide a method and a system for producing an implant placing guide, by which it is possible to produce the implant placing guide without matching a three-dimensional image of an oral cavity and an external-shape image, and thereby it is possible to provide a guide that accurately matches the oral cavity of a patient without an error.

According to the invention made to achieve the object, there is provided a system for producing an implant placing guide, including: a dental-clinic terminal that transmits, to a server, a three-dimensional image acquired by a CT scan in a state where a guide tray filled with an impression material is inserted into an oral cavity of a patient and that receives an implant-placing-guide processing file generated by using the three-dimensional image; a managing server that transmits a plan request signal to one or more preregistered planner terminals when receiving the three-dimensional image from the dental-clinic terminal; and a planner terminal that transmits, to the managing server, a signal of whether or not the plan request signal is accepted when the plan request signal is received from the managing server and that receives and transmits implant planning information corresponding to the three-dimensional image to the managing server when receiving the three-dimensional image from the managing server. The guide tray has one or more markers which are used for identifying a type of guide tray.

DETAILED DESCRIPTION OF THE PREFERRED EMBODIMENTS

The objects, features, and advantages described above will be described below in detail with reference to the accompanying drawings, and thus those who have common knowledge in the art to which the invention belongs can easily embody a technical idea of the invention. In the description of the invention, when detailed description of a known technology related to the invention is deemed to result in blurring the gist of the invention unnecessarily, the detailed description thereof will be omitted. Hereinafter, desirable examples according to the invention will be described in detail with reference to the accompanying drawings. The same reference signs are used to represent the same or similar configurational components, and every combination described in the specification and the following claims can be combined in any manner. Unless otherwise defined, the description has to be understood as follows. A mention of a singular item may include one or more items, and a mention of a singular form may also include a plurality thereof.

Figure 1:
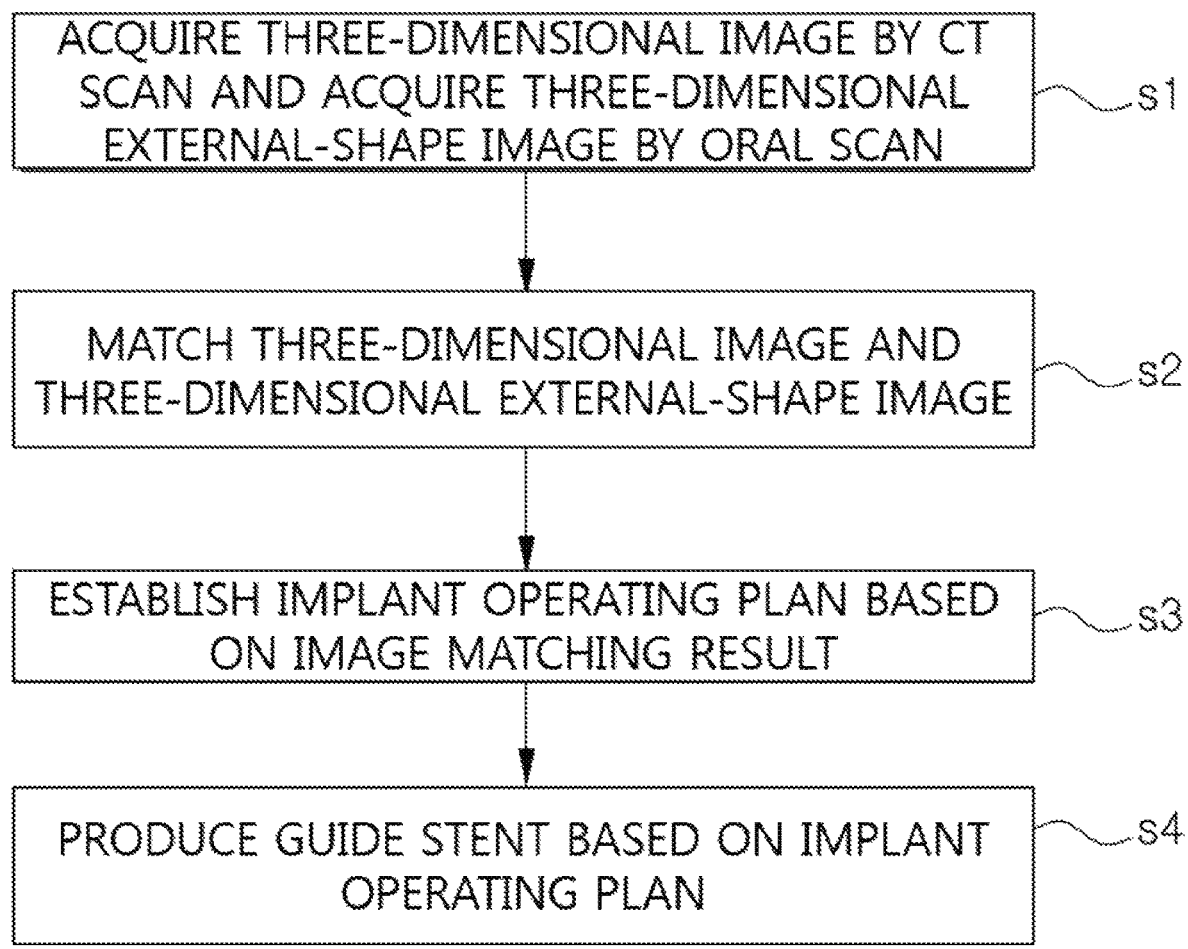
FIG. 1 is a flowchart for illustrating a method for producing a guide stent for an implant in the related art.
Figure 2:
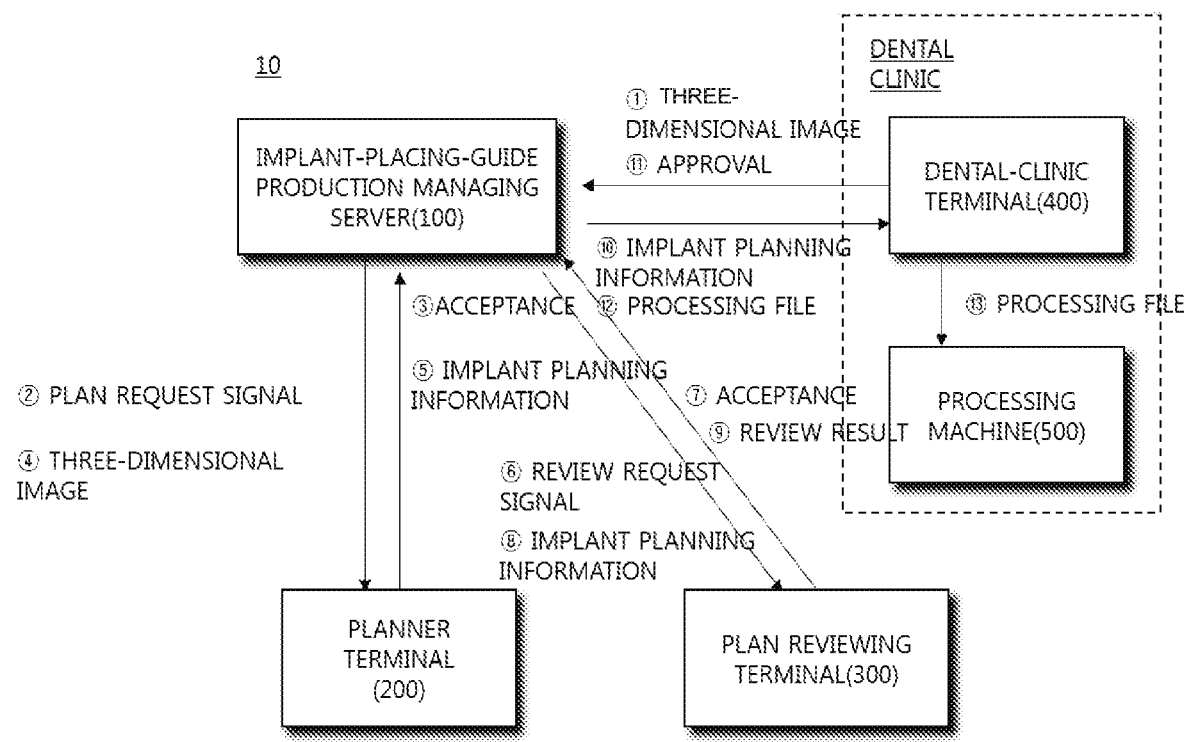
FIG. 2 is a diagram for illustrating a system for producing an implant placing guide according to an example of the invention.

FIG. 2 is a diagram for illustrating a system for producing an implant placing guide according to an example of the invention.

With reference to FIG. 2, the system for producing the implant placing guide according to the example of the invention includes a dental-clinic terminal 400, an implant-placing-guide production managing server 100 (hereinafter, referred to as the "managing server 100"), and a planner terminal 200, and the system may further include a plan reviewing terminal 300 and an implant-placing-guide processing machine 500.

The dental-clinic terminal 400 may be, as a terminal provided in a dental clinic, an electronic device such as a PC, a tablet, or a smartphone in which an application for executing the method for producing the implant placing guide according to the example of the invention is installed. Further, when the method for producing the implant placing guide according to the example of the invention is implemented via Web, the dental-clinic terminal may be an electronic device which can access the Web.

The dental-clinic terminal 400 transmits, to the managing server 100, a three-dimensional image acquired by a CT scan in a state where a guide tray filled with an impression material is inserted into an oral cavity of a patient, and receives an implant-placing-guide processing file from the managing server 100.

The guide tray of the invention may have a similar shape to that of an impression tray used to make a tooth form; however, the guide tray is a known guide tray by which an impression of a teeth shape of the patient is obtained and has markers which are used in i) matching an image of the guide tray and the three-dimensional image, ii) identifying a type of guide tray, and iii) discerning whether or not a sleeve needs to be attached.

The guide tray according to the example of the invention may have one or more markers which performs functions described above, and preferably three or more markers may be formed. The marker may be a radiopaque material and, thus, may be displayed on the three-dimensional image acquired by the CT scan. The marker may be formed on a flat surface of a body of the guide tray in which the impression material is accommodated. In this case, the marker functions as a reference for identifying the guide tray on the three-dimensional image by a surgeon and matching the three-dimensional image and the image of the guide tray. In addition, the marker functions as a reference for a plan of a position, a depth, and a direction at which an implant fixture is placed.

The surgeon performs the CT scan in a state where the guide tray is filled with the impression material, and the tray is inserted into an oral cavity of the patient and is fitted in a site at which an implant operation needs to be performed. The three-dimensional image of the oral cavity is acquired by the CT scan, contains information of an internal tissue such as a crown (upper side of a tooth protruding outside a gum), a root (part joined to an alveolar bone and lower side of a tooth hidden in a gum), or an alveolar bone, and contains an image of the marker of the guide tray. The three-dimensional image does not provide accurate information of the gum. Thus, in the related art, in order to solve such a problem, a three-dimensional external-shape image is acquired by an oral scan, and then matching of a three-dimensional image of an oral cavity and the external-shape image is performed.

However, according to the example of the invention, the oral scan does not need to be performed, and thus the dental-clinic terminal 400 only needs to transmit the three-dimensional image acquired by the CT scan to the managing server. Thus, a process of acquiring oral state information of a patient for an implant operation is remarkably shortened, and this results in effects of reduction in operation time and cost.

The managing server 100 may be, as a computing apparatus that manages production of the implant placing guide according to the example of the invention, a web server or a cloud server. The managing server 100 may transmit a plan request signal to one or more preregistered planner terminals when receiving the three-dimensional image from the dental-clinic terminal, and may generate an implant-placing-guide processing file by using implant planning information when receiving the implant planning information from a planner terminal that accepted the plan request signal. The plan request signal may be a massage (SMS) sent as a text message or may be a push notification transmitted by an application installed in the planner terminal 200.

In this specification, the implant planning information is information of an implant operating plan on the three-dimensional image and may contain at least one of a size of a fixture, a type of fixture, a fixture placing position, a fixture placing depth, whether or not to perform a bone graft, whether or not to perform a maxillary sinus graft, whether or not to perform a gum graft, and a tool order. According to the invention, the implant planning information may be generated in the planner terminal 200, the plan reviewing terminal 300, or the dental-clinic terminal 400 by a user using each terminal, and the implant planning information of the invention may be generated, copied, transmitted, and stored in a form of an implant-planning information file (STL file and/or PDF file).

An operation of the managing server 100 will be described below in detail with reference to FIG. 3.

A system 10 for producing the implant placing guide according to the example of the invention may include the planner terminal 200. The planner terminal 200 may be a terminal possessed by a user who is qualified for implant planning or a terminal possessed by a user who is certified to have both the implant planning qualification and a dentist qualification. The planner terminal 200 may transmit, to the managing server, a signal of whether or not the plan request signal is accepted when the plan request signal is received from the managing server and may receive and transmit implant planning information corresponding to the three-dimensional image to the managing server when receiving the three-dimensional image from the managing server.

The system 10 for producing the implant placing guide according to the invention may include the plan reviewing terminal 300. The plan reviewing terminal 300 is a terminal possessed by a user who is certified to have the dentist qualification. The system 10 may not include the plan reviewing terminal 300 when the planner terminal 200 is possessed by a user who is certified to have both the implant planning qualification and the dentist qualification. The plan reviewing terminal 300 may transmit, to the managing server, a signal of whether or not a review request signal is accepted when the review request signal is received from the managing server and may receive and transmit a review result corresponding to the implant planning information to the managing server when receiving the implant planning information from the managing server.

An acceptance signal may be transmitted in response to a touch or a click of the user on one link of a massage (SMS) which is displayed by the terminal 200 or 300, a touch or a click on an acceptance button or a link which is displayed on a web page provided via a web server 100, or a touch or a click on an acceptance button of an application installed in the terminal 200 or 300, and a way of transmitting the signal of whether or not the review request signal is accepted to the server 100 is not limited thereto.

The system 10 for producing the implant placing guide of the invention may include the implant-placing-guide processing machine 500 (hereinafter, referred to as the "processing machine 500" for convenience of description). The processing machine 500 according to the example of the invention is provided in a dental clinic from which the three-dimensional image is transmitted, may identify a position of a jig and a guide hole corresponding to the type of guide tray by using an implant-placing-guide processing file when receiving the implant-placing-guide processing file from the managing server or the dental-clinic terminal, and may form the guide hole at the guide tray by using the identified jig. The guide hole may be formed through machining work by a machine tool such as a milling machine. The implant-placing-guide processing file includes the image of the guide tray in which the location of the guide hole is marked. The processing file may or may not include the implant planning information on the image of the guide tray. Further, a metal sleeve may or may not be attached to the guide hole. When the sleeve is attached, the processing file may include information of a position of the sleeve and a region which is removed by the attaching of the sleeve.

In other words, when the surgeon has the processing machine 500 and the surgeon (dental-clinic terminal) acquires and transmits the three-dimensional image of the oral cavity of the patient to the managing server, the surgeon may receive the implant-placing-guide processing file within several minutes to one to two hours, and the implant-placing-guide processing file is transmitted to the processing machine 500—this transmission does not need to be performed when the implant-placing-guide processing file is directly transmitted to the processing machine 500. When a guide tray having an impression of the patient is installed in the processing machine 500, the processing machine 500 automatically identifies the pre-generated guide tray, a position of the guide hole at the guide tray, and a jig to be used and just forms the guide hole, and thus the implant placing guide is obtained within several minutes. Besides, the implant placing guide according to the example of the invention is acquired by filling the guide tray with the impression material, fitting in teeth arrangement and a gum of the patient, and then hardening the impression material. Hence, the implant placing guide is characterized by having the impression of a teeth shape of the patient and thus is settled in the teeth arrangement and the gum of the patient without an error. Thus, it is not only easy to perform the implant operation, but also a problem of unfitting of the implant placing guide in the oral cavity of the patient does not arise. Accordingly, there is no need to perform correction, and an effect of an increase in satisfaction of the patient is achieved.

In the example of the invention, the implant-placing-guide processing file may be recognized by the processing machine 500 (or the milling machine) and may include an Numerical Control (NC) file that can be recognized in the CAM program which is a processing machine driving program.

Hereinafter, with reference to the drawings, systems (10) for producing an implant placing guide according to various examples of the invention will be described.

EXAMPLE 1

Figure 3:
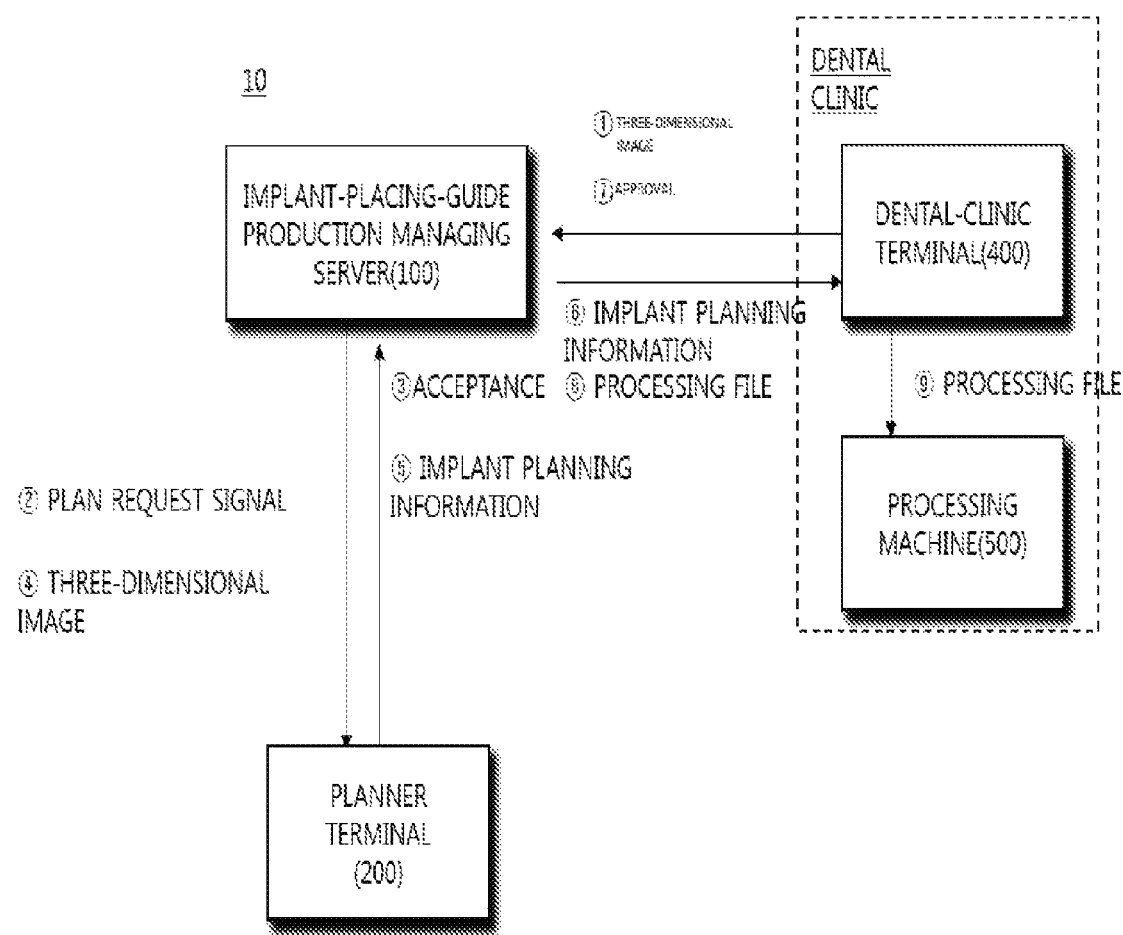
FIG. 3 is a diagram for illustrating a system for producing an implant placing guide according to another example of the invention.

Case of Configuring a System with Dental-Clinic Terminal, Planner Terminal, and Managing Server FIG. 3 illustrates an example in which a user of the planner terminal possesses both the implant planning qualification and the dentist qualification. The implant operation has to be finally confirmed by a dentist, and thus it is assumed that the user of the planner terminal possesses the dentist qualification in the example.

Figure 4:
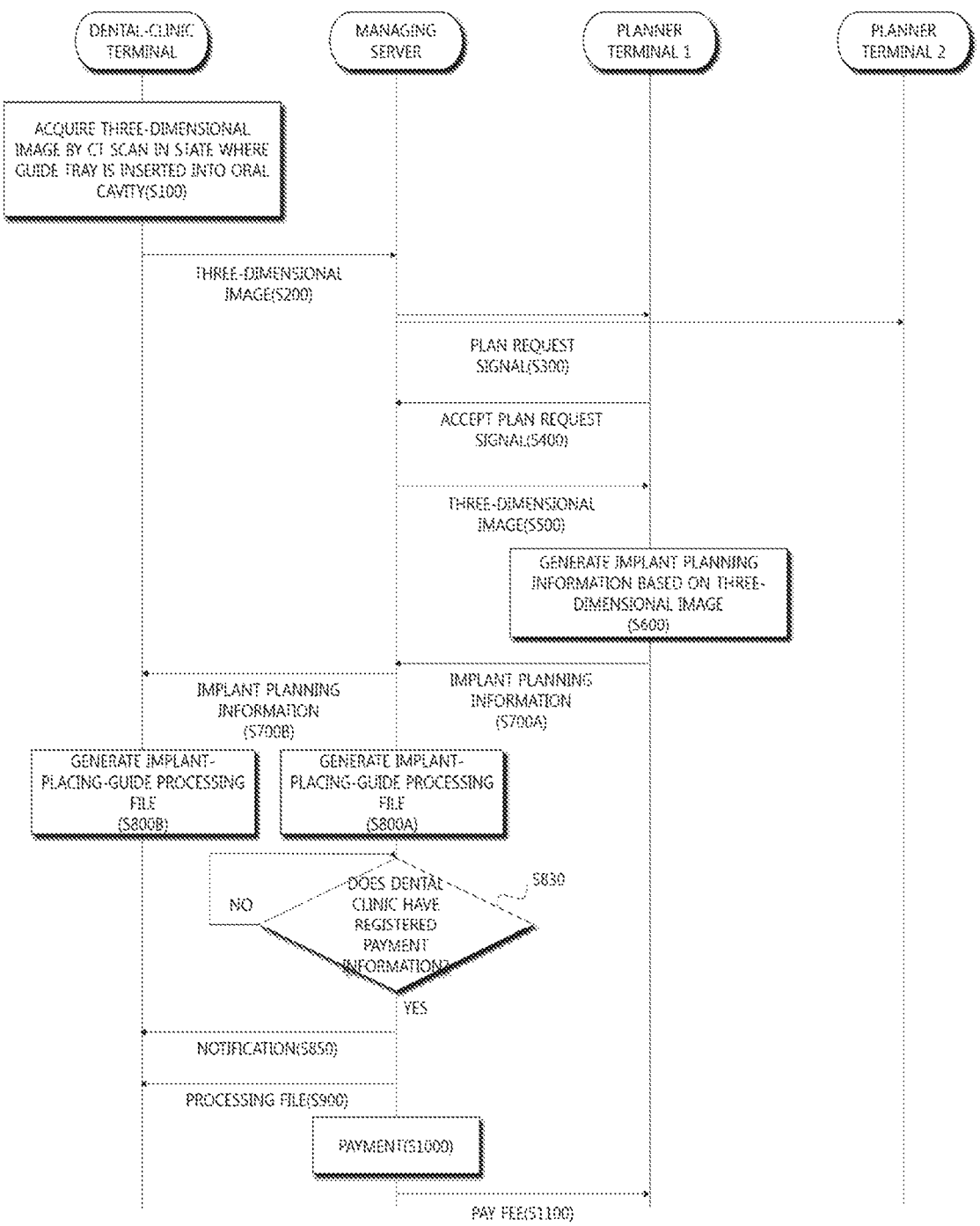
FIG. 4 is a flowchart for illustrating a method for producing the implant placing guide according to the example of the invention.

With reference to FIG. 4, the dental-clinic terminal acquires the three-dimensional image obtained by the CT scan in a state where the guide tray of the invention is inserted into the oral cavity (S100). This means that the dental-clinic terminal receives the three-dimensional image acquired by the CT scan from a scanning apparatus. Next, the dental-clinic terminal may transmit the three-dimensional image to the managing server. Transmission to the managing server includes upload of the three-dimensional image. The three-dimensional image transmitted from the dental-clinic terminal to the managing server may include identification information (code of the dental clinic, name of the dental clinic, name of the surgeon, or the like) of the dental-clinic terminal and information (name, age, and gender of the patient, other personal information necessary for the implant operation, or the like) of the patient.

When the managing server receives the three-dimensional image (S200), that is, when the three-dimensional image and other information are uploaded, the managing server can transmit the plan request signal to one or more preregistered planner terminals (S300). As described above, the plan request signal can be transmitted in a manner of notifying the planner terminal of an uploading event.

The planner terminal is a terminal possessed by a planner who has both the implant planning qualification and the dentist qualification and may be a terminal device in which an application for supporting the method for producing the implant placing guide according to the example of the invention is installed. Planners can register planner information in the managing server in advance via the application or the web, and user information (name of a planner, qualification of the planner, record accumulated as the planner, or the like) of the planner terminal can be transmitted to the managing server when the planner information is registered. After the managing server checks the qualification of the planners, the managing server assigns a different rank for each of the planners. For example, a level A is assigned to a planner who has only the implant planning qualification, and a level B is assigned to a planner who has both the implant planning qualification and the dentist qualification. In other words, the planners can be classified into one or more groups depending on skills of the planners, and criteria of classification can change depending on setting by a manager.

As another example, the managing server can classify planners depending on records accumulated by the planners or can classify planners depending on feedbacks (points or review) of the dental-clinic terminal.

A planner can access the managing server by using an ID and a password registered in advance regardless of a terminal to be used by the planner, can specify a time as the planner wants and receive the plan request signal at the time, and can set whether to receive or reject the plan request signal.

In Step 300, when the planner receives the plan request signal, the planner can determine whether or not to accept the plan request signal and input a result thereof. When the planner inputs a selecting input of acceptance of the plan request signal to the planner terminal, the planner terminal can transmit, to the managing server, a signal indicating that the plan request signal is accepted (S400).

When the managing server receives acceptance of the plan request signal, the managing server can transmit the three-dimensional image to the planner terminal that accepted the plan request signal (S500). The acceptance of the plan request signal and the transmission of the three-dimensional image mean conclusion of a contract between the managing server and the planner, and Step 500 can be executed by an operation in which the planner accesses the managing server by using the planner terminal and downloads a three-dimensional image file (CT file, dicom file).

In a case in which acceptance of the plan request signal is received from a plurality of planner terminals, the managing server can select one or a plurality of planner terminals in accordance with a preset criterion. For example, the managing server can select a planner terminal based on an arrival order of signals indicating the acceptance of the plan request signal to the managing server or can select a planner terminal holding the fewest records or the most records of the implant planning by using the preregistered planner information. The criterion of selection of the planner terminal can change depending on setting by the manager, and whether to select one planner terminal or select a plurality of planner terminals can also change depending on setting by the manager.

The planner terminal that receives the three-dimensional image generates the implant planning information based on the three-dimensional image (S600). The implant planning information is information of the implant operating plan on the three-dimensional image may contain, at least one of a size of a fixture, a type of fixture, a fixture placing position, a fixture placing depth, whether or not to perform a bone graft, whether or not to perform a maxillary sinus graft, whether or not to perform a gum graft, and a tool order. The information such as the size of the fixture or the type of fixture may be input to the planner terminal via an input device such as a touch screen, a keyboard, a mouse, or a touch pad which is provided or connected to the planner terminal, and the planner terminal may generate the implant planning information by using the input information. The implant planning information of the invention may be generated, copied, transmitted, and stored in a form of an implant planning information file (STL file and/or xml or PDF file). Further, the implant planning information generated by the planner terminal may be an encoded file, and decoding of the encoded file may be set to be performed only by the managing server.

The planner terminal may transmit the generated implant planning information to the managing server (S700A). Transmission of the implant planning information to the managing server includes an operation in which the planner terminal uploads the implant planning information (STL file and/or xml or PDF file) in a web server or a cloud server corresponding to the managing server. Such upload may be automatically performed when the planner clicks an implant planning information generation completion button at the implant planning information generating software of the planner terminal.

The managing server can check classification information of the planner terminal that transmits the implant planning information to the managing server, although not illustrated in the drawing. When the planner terminal is verified as the terminal possessed by the planner who has both the implant planning qualification and the dentist qualification, the managing server may generate the implant-placing-guide processing file by using the implant planning information (S800).

In Step 800, the implant planning information can be converted into a file format which can be recognized by the processing machine. For example, in Step 800A, the managing server 100 can convert the implant planning information into an NC file which can be recognized by the processing machine 500. The implant planning information may be a file format (for example, a CAD file or a stereo lithography (STL) file) supported by the web or the application provided by the managing server, and conversion of the implant planning information into the implant-placing-guide processing file (for example, NC file) may be an unique privilege of the managing server. The managing server may generate the implant-placing-guide processing file by using the CAM program that is executed only in the web or a cloud.

The implant planning information may be encoded to be converted into the file format, which can be recognized by the processing machine that performs processing, only by the managing server when the implant planning information is generated. Otherwise, the implant planning information may be a file which can be generated only by the web or the application provided by the managing server of the invention. Further, the implant-placing-guide processing file according to the example of the invention may be a file having a format which can be executed only by a predesignated processing machine.

The conversion of the implant planning information into the implant-placing-guide processing file being an unique privilege of the managing server is to establish a profit model based on generation (or output) of the implant-placing-guide processing file by the managing server.

As an example, when the implant-placing-guide processing file is generated (S800), the managing server can verify whether or not payment information (card information, account information, or the like) of a dental clinic which requested the implant-placing-guide processing file is registered (S830). In a case of a dental clinic of which the payment information such as the card information or the account information is registered, the dental clinic can be notified of generation of the processing file (S850), and the processing file can be transmitted to the dental clinic (S900). Step 900 includes a method in which the dental-clinic terminal accesses a web server 100 and downloads a file. Then, after the file is transmitted, a cost corresponding to transmission of the processing file can be paid by using the payment information (S1000). Step 1000 may be executed before Steps 850 and 900.

As a result of determination in Step 830, when the payment information of the dental clinic that requested the guide processing file is not registered in the managing server 100, the managing server 100 can block the access of the dental-clinic terminal to the server 100. For example, in a case where the managing server is a web server, the managing server blocks the access of the dental-clinic terminal, of which the payment information is not registered, to the web server or does not assign access privilege to the dental-clinic terminal, and thereby it is possible to limit the download of the guide processing file.

As another example, the managing server may transmit the implant-placing-guide processing file to the dental-clinic terminal or the processing machine (S900) and may count the number of times of output or transmission of the implant-placing-guide processing file and claim a plan fee to the dental-clinic terminal by the number of times (S1000). As an example different from the examples illustrated in the drawings, a claim for a service charge may be performed before Step 800 of generating the implant-placing-guide processing file or Step 900 of transmitting the implant-placing-guide processing file, and it is possible to execute Step 800 or 900 when the service charge corresponding to the claim for the costs is deposited from the dental-clinic terminal.

When the service charge is deposited, the managing server can remit an amount obtained by subtracting a preset fee from the service charge to an account linked to a planner terminal 1 that executes the implant planning (S1100).

As still another example, when implant planning information generated by the planner terminal is uploaded in the managing server (S700A), the dental-clinic terminal can download the implant planning information (S700B). Then, the dental-clinic terminal can directly generate (convert) the implant-placing-guide processing file using the implant planning information by using software installed in the dental-clinic terminal (S800B). Here, the uploaded implant planning information may be an encoded STL, xml, and/or PDF file, the encoded file can be decoded in the managing server, and the dental-clinic terminal can download the implant planning information which is not encoded in Step 700B. In the example, it is desirable that both software for generating the implant planning information and software for converting the implant planning information into the implant-placing-guide processing file be installed in the dental-clinic terminal.

EXAMPLE 2

Figure 5:
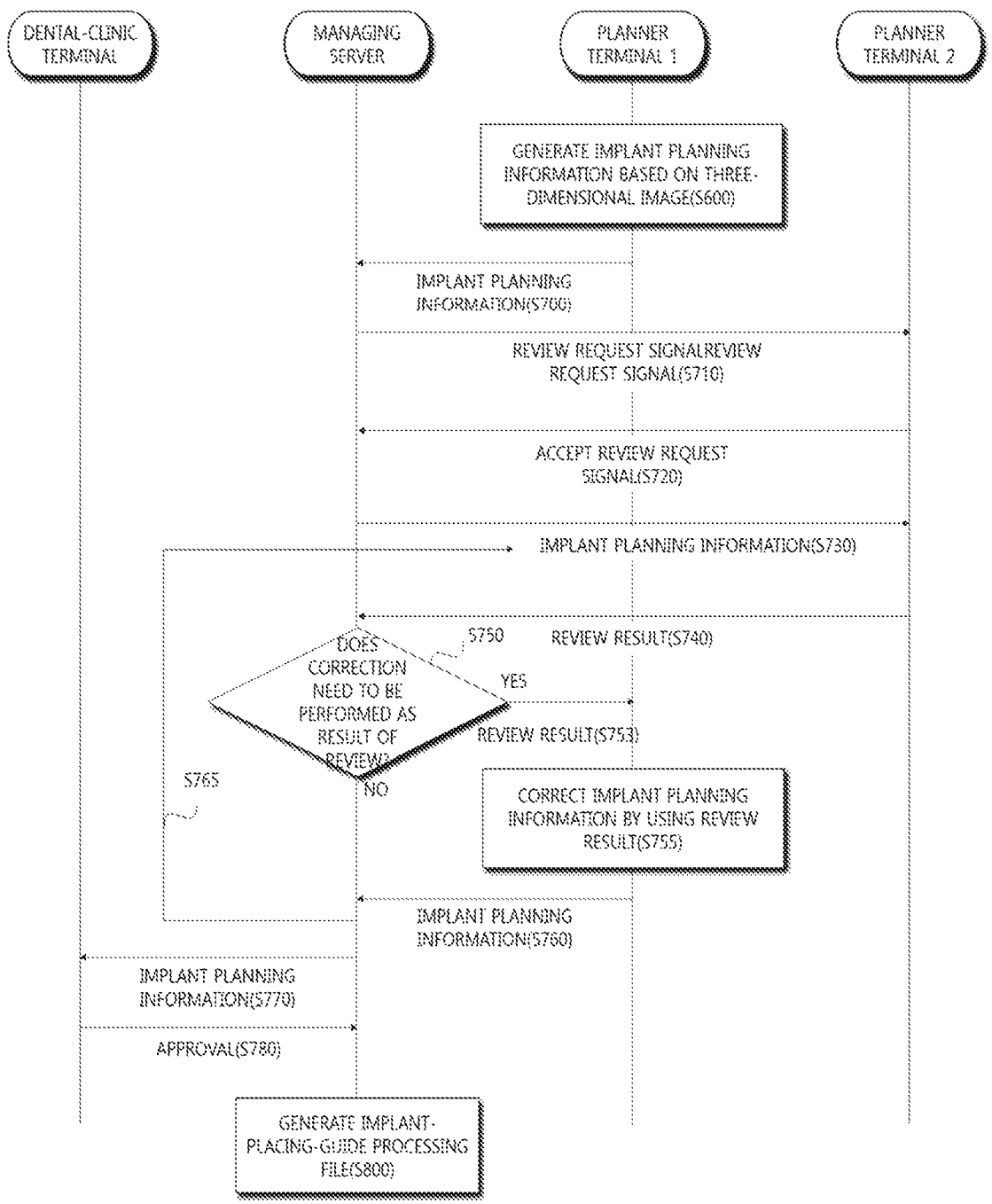
FIG. 5 is a flowchart for illustrating the method for producing the implant placing guide according to the example of the invention.

Case of Configuring a System with Dental-Clinic Terminal, Planner Terminal, Plan Reviewing Terminal, and Managing Server As illustrated in FIG. 2, an example of a case in which the system is configured of the dental-clinic terminal 400, the planner terminal 200, the plan reviewing terminal 300, and the managing server 100 is described with reference to FIG. 5. The planner terminal in the example is assumed to be a terminal possessed by a user who is certified to have only the implant planning qualification, and the plan reviewing terminal is assumed to be a terminal possessed by a user who is certified to have the dentist qualification. Some steps omitted in FIG. 5 can be provided with reference to FIG. 4 (assuming that the planner terminal in FIG. 5 is the planner terminal 1 in FIG. 4).

The implant planning information generated by the planner having only the implant planning qualification needs to be confirmed by the user having the dentist qualification. Thus, when the planner terminal that accepts the plan request signal corresponding to transmission of the plan request signal in Step 300 is a terminal possessed by the planner who is certified to have only the implant planning qualification, the managing server may additionally perform a step of reviewing the implant planning information generated in the step such as Step 710 or 760 in FIG. 5.

Describing again from Step 600, the managing server may receive the implant planning information from the planner terminal and may transmit a review request signal to one or more preregistered plan reviewing terminals (S710). When the review request signal is accepted by any one of a plurality of plan reviewing terminals which receive the review request signal (S720), the managing server may transmit the implant planning information to the plan reviewing terminal that accepted the review request signal (S730). Steps 720 and 730 of selecting the plan reviewing terminal can be executed in a method similar to that in the example described in Step 300 and 400 in FIG. 4. In other words, the acceptance of the plan request signal and the transmission of the implant planning information can be understood to mean a conclusion of a contract between the managing server and the plan reviewing terminal.

The plan reviewing terminal may transmit a review result to the managing server (S740). The review result may include a correction opinion and a correction item for the implant planning information and may include an opinion of confirming that the implant plan is appropriately designed. The managing server may check the review result (S750) and may transmit the review result to the planner terminal (S753) when the review result includes the correction opinion.

The planner terminal that receives the review result including the correction opinion may correct the implant planning information by using the review result (S755); however, the managing server may correct the implant planning information by reflecting the review result internally when the planner is present in a center that possesses the managing server. Otherwise, the managing server may actively correct the implant planning information by reflecting the review opinion by using a machine learning framework learned using many items of data.

The corrected implant planning information is transmitted to the managing server again (S760), the managing server transmits the implant planning information to the plan reviewing terminal again (S765), and correction and review can be repeated until correction is unnecessary.

The managing server can transmit the implant planning information to the dental-clinic terminal (S770) when there is no correction item as a result of review. When the implant planning information is approved by the dental-clinic terminal (S780), it is possible to generate the implant-placing-guide processing file (S800). For reference, Steps 770 and 780 can be executed before the execution of Step 800 even in the example of FIG. 4. In other words, after the implant planning information is checked by the dental-clinic terminal, the implant-placing-guide processing file is generated, and thereby it is possible to minimize unnecessary conversion of the file.

Figure 6:
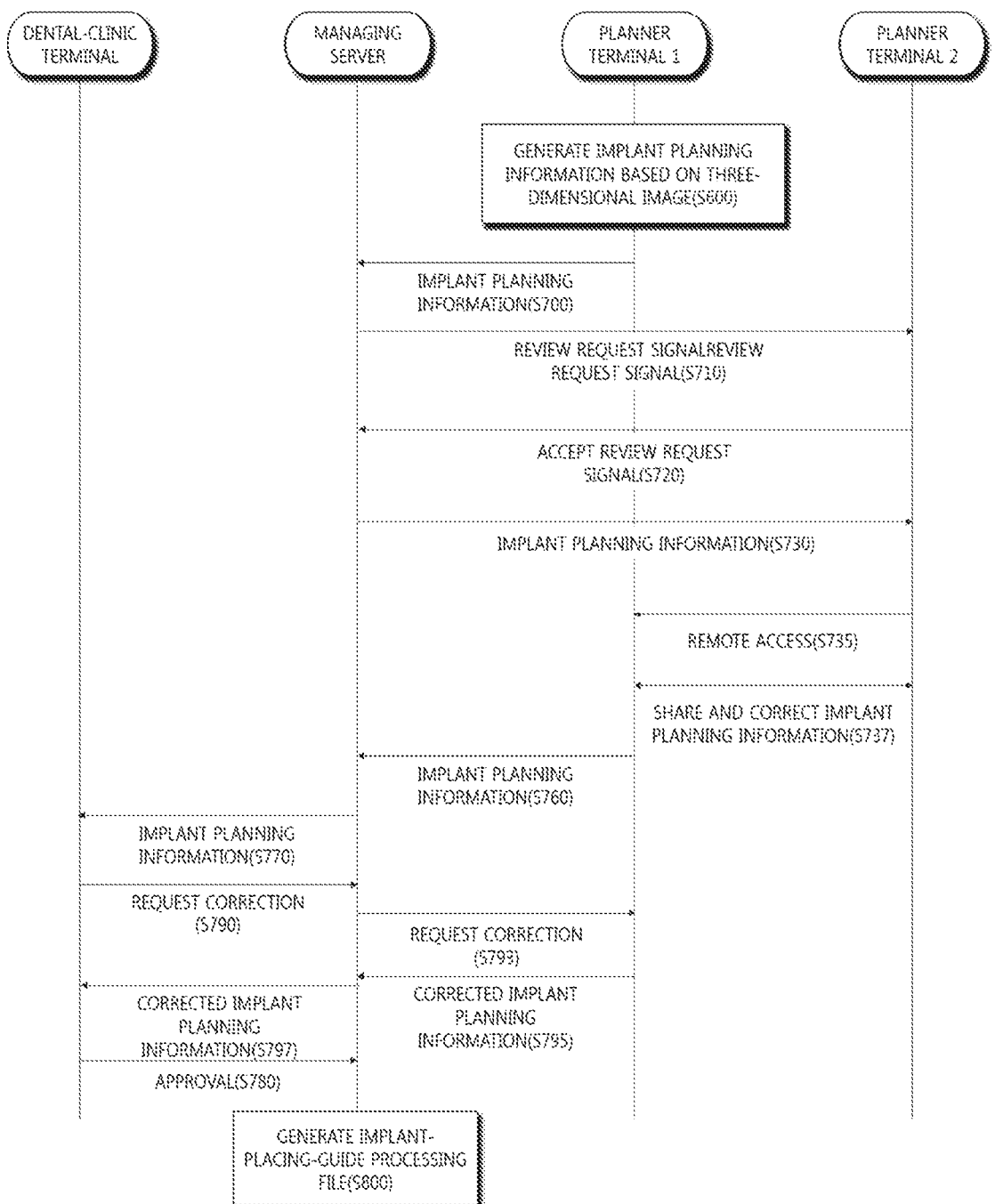
FIG. 6 is a flowchart for illustrating the method for producing the implant placing guide according to the example of the invention.
Figure 10:
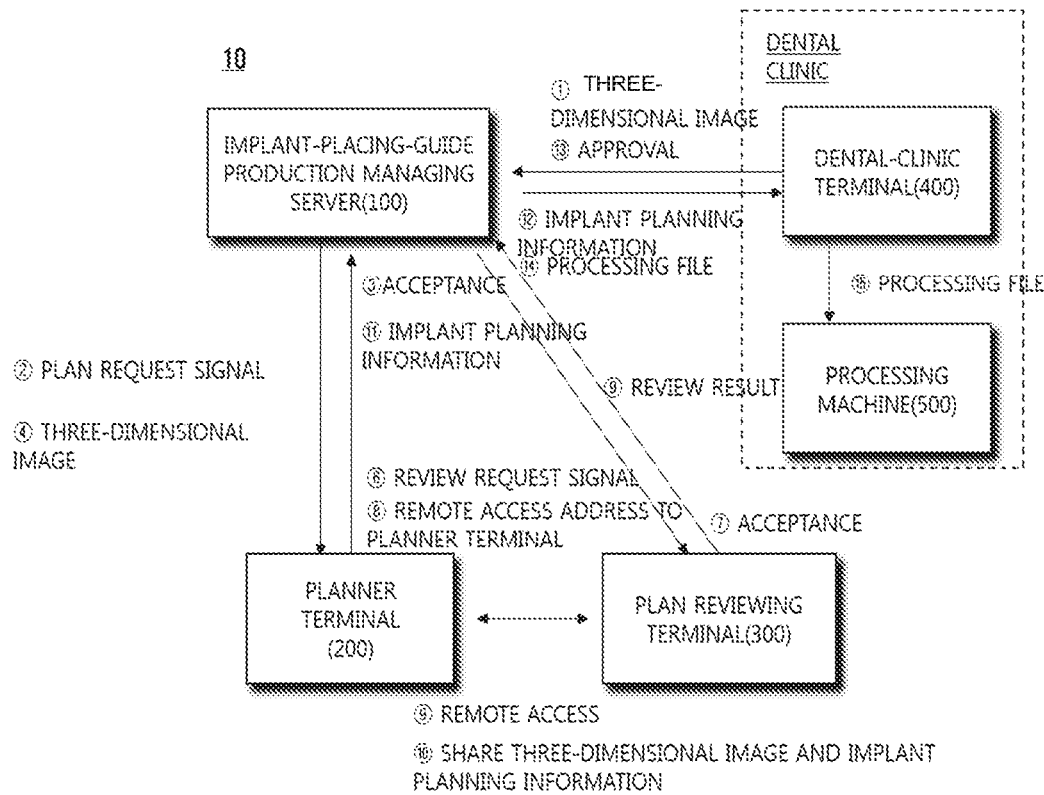
FIG. 10 is a diagram for illustrating the system for producing the implant placing guide according to the example of the invention.

When the managing server transmits the implant planning information to the plan reviewing terminal in Step 730, the managing server transmits the implant planning information and a remote access address which is used to share and correct the three-dimensional image in real time with the planner terminal that generates the implant planning information, and thereby it is possible to perform correction and check in real time between the planner terminal and the plan reviewing terminal without Steps 740 to 760. Such an example is illustrated in FIG. 6. With reference to FIG. 6, the plan reviewing terminal that receives the remote access address can access to the planner terminal remotely (S735) and can share and correct the implant planning information (S737). In this case, it is not necessary to transmit and receive the implant planning information via the managing server, and thus it is possible to significantly shorten a correction and confirmation step. Sharing and correcting of the implant planning information via remote access can also be performed via the web or application for producing the implant placing guide according to the invention or may be performed via another application for supporting the remote access. FIG. 10 additionally illustrates the system for producing the implant placing guide which is illustrated as the example.

FIG. 6 illustrates an example of a case in which the dental-clinic terminal transmits a correction request (S790). When the dental-clinic terminal replies to the received implant planning information with the correction request rather than the approval thereto as in Step 780 illustrated in FIG. 5 (S790), the managing server can transmit the correction request to the planner terminal (S793) and can receive and transmit the implant planning information in which the correction request is reflected to the dental-clinic terminal (S797), and Steps 793 to 797 can be repeated until the approval from the dental-clinic terminal is received.

Similarly to the example in FIG. 4, in the examples in FIGS. 5 and 6, it is possible to claim the service charge to the dental-clinic terminal before or after the implant-placing-guide processing file is generated (S1000), a preset planning fee can be remitted to the account linked to the planner terminal, and a preset plan review fee can be remitted to an account linked to the plan reviewing terminal (S1100).

EXAMPLE 3

Case of Configuring a System with Terminal and Processing Machine

Figure 7:
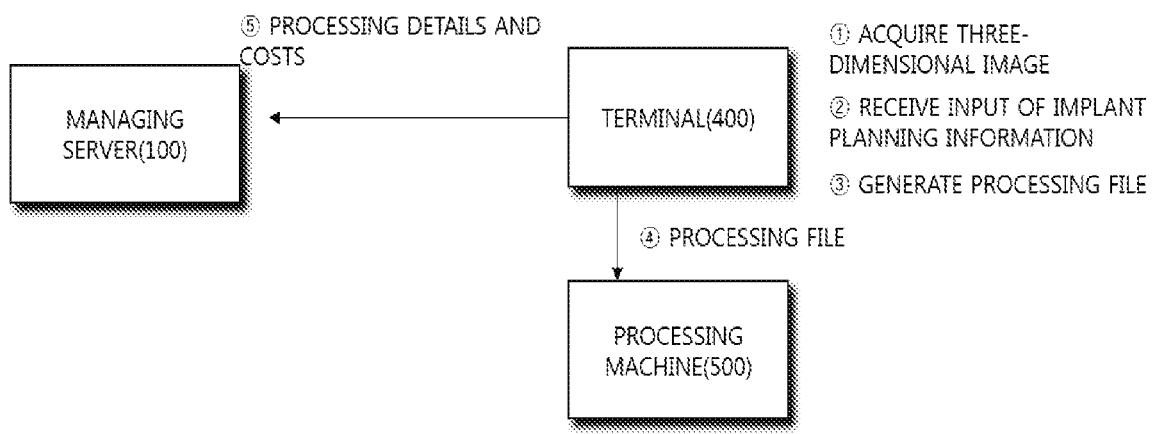
FIG. 7 is a diagram for illustrating the system for producing the implant placing guide according to the example of the invention.
Figure 8:
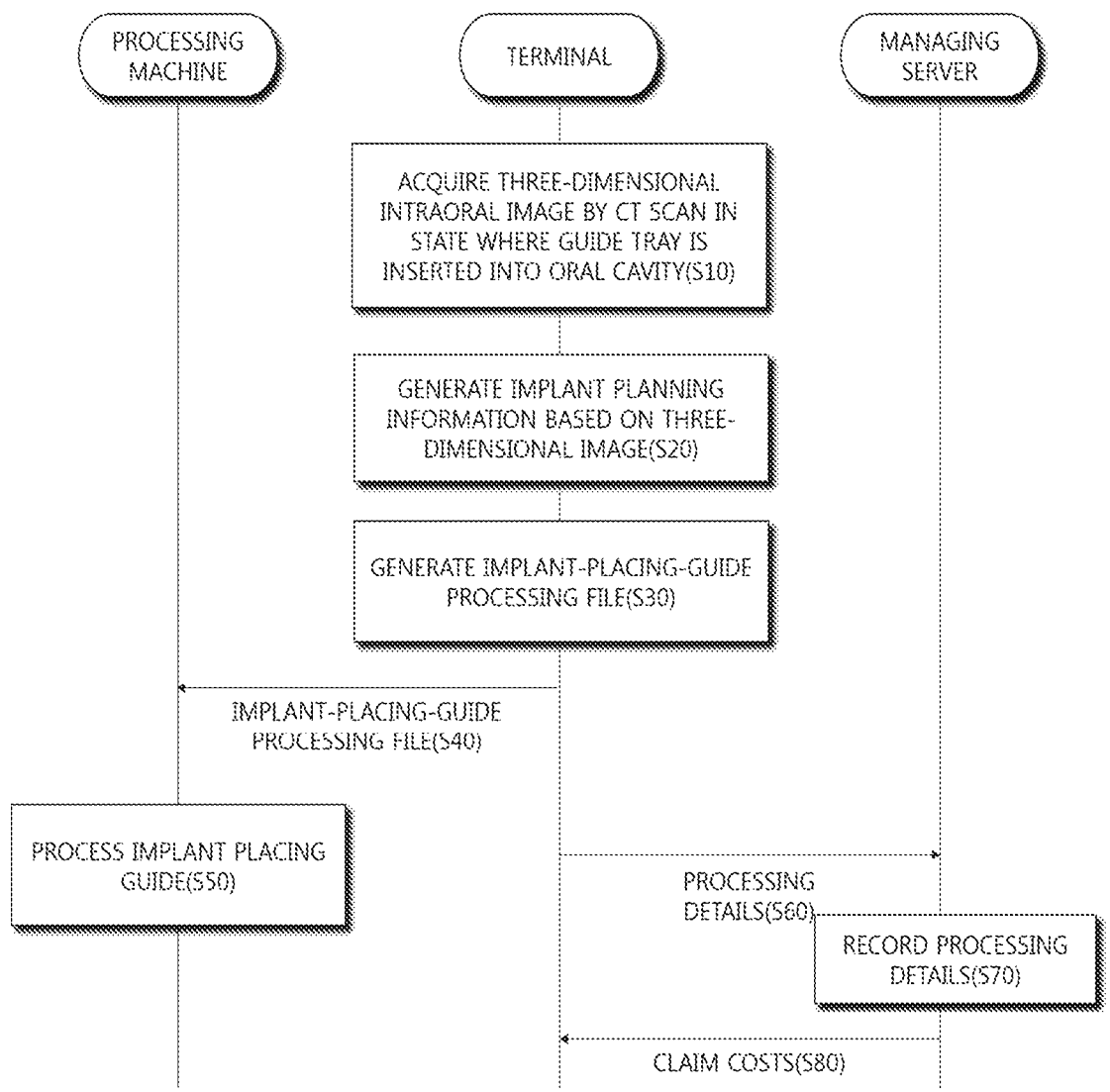
FIG. 8 is a flowchart for illustrating the method for producing the implant placing guide according to the example of the invention.

An example illustrated in FIGS. 7 and 8 is an example of i) a case in which the entire process of the implant operation is performed in the center that possesses the managing server (in this case, the terminal can be understood to mean a computing apparatus which is used in the center, and the managing server can be understood to mean a server possessed by the center), ii) a case of configuring a system with the dental-clinic terminal and the processing machine in the dental clinic (in the example in FIGS. 7 and 8, the managing server can be omitted), and iii) a case of configuring a system with the dental-clinic terminal and the processing machine which are possessed by the dental clinic and an external managing server (in this case, the terminal can be understood to mean the dental-clinic terminal, and the managing server can be understood to mean a server—a web server or a cloud server—possessed by the center).

The terminal can acquire the three-dimensional intraoral image acquired by the CT scan in a state where the guide tray is inserted into an oral cavity of a patient (S10). Acquisition of the three-dimensional image includes receiving of the three-dimensional image from a CT scanning apparatus and receiving of the three-dimensional image via wired or wireless network The terminal may receive an input of the implant planning information from a terminal of the user (S20). For example, the user can draw the implant operating plan on the three-dimensional image via an input unit connected to the terminal and also can write down the size of the fixture, the type of fixture, the fixture placing position, the fixture placing depth, whether or not to perform a bone graft, whether or not to perform a maxillary sinus graft, whether or not to perform a gum graft, a tool order, or the like. As described above, the implant planning information may be generated in a STL file format, and the STL file generated via a CAD program may further include the PDF or xml file that includes an operation method and/or operation information.

In this case, when the implant planning information is input, the terminal can locate a guide hole on the image of the guide tray in accordance with the implant planning information. Then, it is possible to generate the implant-placing-guide processing file including the image of the guide tray in which the guide hole is located (S30). Generation of the guide processing file can be achieved through the conversion of the STL file which is the implant planning information into the NC file. The file conversion can be achieved via the CAM program that is executed in the web or cloud server. In this case, the terminal uploads the guide processing file in the web or cloud server, and when the file is converted, it is possible to convert the file in a method of downloading the converted file. As still another example, the STL file can be directly converted via the CAM program installed in the terminal, the CAD program and the CAM program which receive an input of the implant planning information can be executed by linking to each other.

The generated implant-placing-guide processing file is transmitted to the processing machine (S40), and the processing machine machines the implant placing guide by using the received processing file (S50). The processing of the implant placing guide can be performed by a simple operation of forming the guide hole at the guide tray inserted into the oral cavity of the patient, and it is possible to shorten a processing time because 3D printing or accurate work does not need to be performed.

Figure 9:
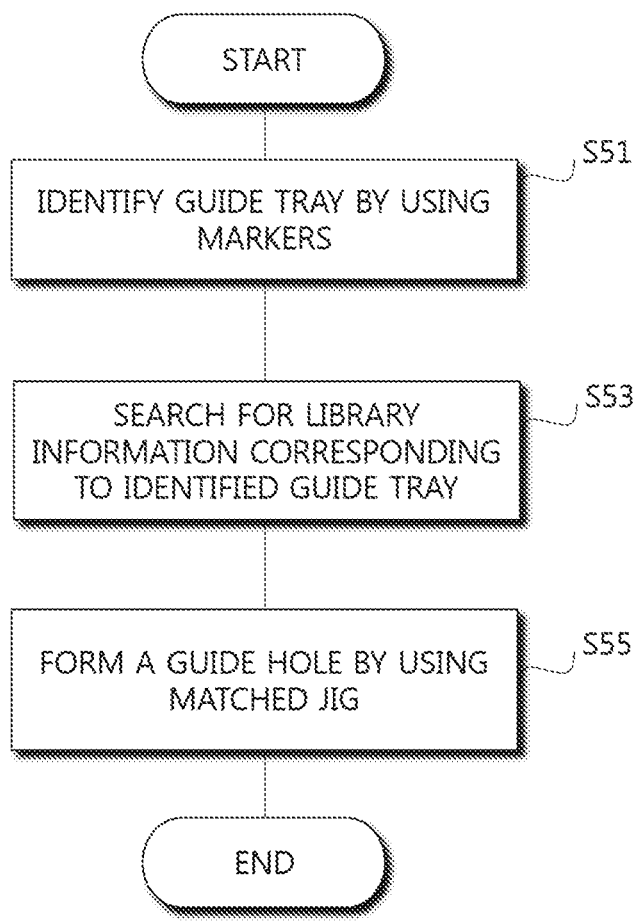
FIG. 9 is a flowchart for illustrating a method for producing an implant placing guide by a processing machine according to the example of the invention.

When Step 50 is further described with reference to FIG. 9, the processing machine can identify the guide tray by using the number of markers, a shape of the marker, an angle formed by the plurality of markers, or the like of the guide tray which are included (appear on the three-dimensional image) in the implant-placing-guide processing file (S51). The guide tray has various shapes and sizes corresponding to an oral structure of the patient. The guide tray used in the invention may have an identification code unique for each type of guide tray and may have unique marker information. In other words, the number and shape of markers and the angle and a shape formed by the plurality of markers, which appear on the three-dimensional image can match each unique identification number.

Figure 11:
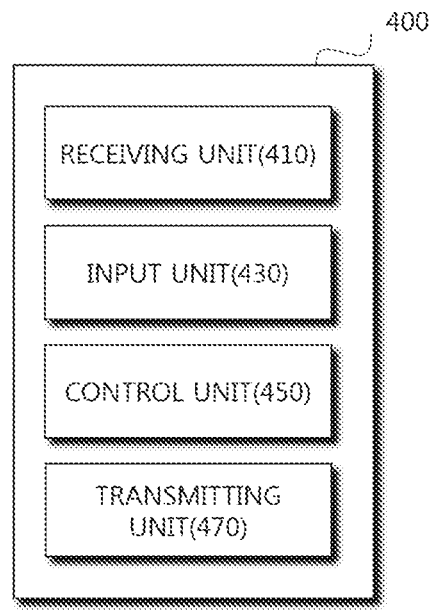
FIG. 11 is a diagram for illustrating a configuration of a dental-clinic terminal according to the example of the invention.

That is, with reference to FIG. 11, the dental-clinic terminal 400 of the invention may comprise a receiving unit 410 receiving the three-dimensional intraoral image of the patient acquired by a CT scan in a state where the guide tray filled with the impression material is inserted into the oral cavity of the patient and an input unit 430 in which the implant planning information on the three-dimensional image is input. In addition, the dental-clinic terminal 400 may also comprise a control unit 450 matching the three-dimensional image and an image of the guide tray by using the marker information of the guide tray, which is contained in the three-dimensional image, locating the guide hole on the image of the guide tray according to the implant planning information, and generating the implant-placing-guide processing file by using the image of the guide tray in which the guide hole is located, and a transmitting unit 470 transmitting implant-placing-guide processing file to the processing machine.

When the processing machine of the invention identifies the guide tray, the processing machine can search for a tray library and a jig library corresponding to the identified guide tray (S53). The tray library is a database including external-shape information and identification information of various guide trays, and the jig library is a database including external-shape information and identification information of a processing machine jig suitable to be used for each guide tray. The processing machine can form the guide hole by using the jig which matches the identified guide tray (S55).

Subsequently, processing details in the terminal can be transmitted to the managing server (S60), the managing server records the processing details (S70), and it is possible to claim costs thereof to the dental-clinic terminal (S80). However, Steps 60 to 80 are additionally provided and thus can be omitted.

Finally, the method for producing the implant placing guide according to the example of the invention is described.

An electronic device equipped with a processor acquires the three-dimensional intraoral image of the patient by a CT scan in a state where the guide tray filled with the impression material is inserted into the oral cavity of the patient, and the electronic device receives the input of the implant planning information on the three-dimensional image. Next, the electronic device matches the three-dimensional image and an image of the guide tray by using the marker information of the guide tray, which is contained in the three-dimensional image.

The electronic device locates the guide hole on the image of the guide tray according to the implant planning information and generates the implant-placing-guide processing file by using the image of the guide tray in which the guide hole is located. The electronic device forms the guide hole at the guide tray by using the implant-placing-guide processing file, and the guide tray has an impression of a teeth shape of the patient.

When locating the guide hole, the electronic device can generate an image of the guide hole on the image of the guide tray with a vertical axis of an implant fixture as a reference, the vertical axis being contained in the implant planning information, and the electronic device can locate a removing region around the guide hole, the removing region being provided to insert the jig.

Further, the electronic device can remit a cost corresponding to the number of times of generation of the implant-placing-guide processing file to a preset server account.

As described above, according to the invention, a time for producing an implant placing guide is significantly shortened, and thus convenience of a patient remarkably improves.

In addition, according to the invention, a profit by every performer participated in producing of the implant placing guide can easily generate a profit, and a fair profit distribution can be achieved.

In addition, according to the invention, it is easy to plan and correct the implant placing guide.

In addition, according to the invention, it is possible to produce the implant placing guide without matching a three-dimensional image of an oral cavity and an external-shape image, and thereby it is possible to provide, to a patient, a guide that accurately matches the oral cavity of the patient without an error.

In this specification, some omitted examples can be applied in a similar manner when a main performer is the same. In addition, it is possible for those who have common knowledge in the art to which the invention belongs to perform various substitutions, changes, and modifications of the invention without departing from the technical idea of the invention, and thus the invention is not limited to the examples and the accompanying drawings described above.

While the present invention has been described with respect to the specific embodiments, it will be apparent to those skilled in the art that various changes and modifications may be made without departing from the spirit and scope of the invention as defined in the following claims.

What is claimed is:

1. A method for managing production of an implant placing guide by an implant-placing-guide production managing server, the method comprising:
   step a of receiving, from a dental-clinic terminal, a three-dimensional intraoral image acquired by a CT scan in a state where a guide tray filled with an impression material is inserted into an oral cavity of a patient;
   step b of transmitting a plan request signal to one or more preregistered planner terminals;
   step c of transmitting the three-dimensional image to a first planner terminal which accepts the plan request signal; and
   step d of receiving implant planning information generated based on the three-dimensional image from the first planner terminal,
   wherein the guide tray has one or more markers which are used for matching an image of the guide tray and the three-dimensional image and has an impression of a teeth shape of the patient.

2. The method for managing production of an implant placing guide according to claim 1, further comprising:
   step e of generating an implant-placing-guide processing file in which a location of a guide hole is marked on the image of the guide tray by using the implant planning information; and
   step f of transmitting the generated implant-placing-guide processing file to the dental-clinic terminal or an implant-placing-guide processing machine provided in a dental clinic, wherein the step e includes
a step of matching the three-dimensional image and the image of the guide tray by using the markers,
a step of locating the guide hole on the image of the guide tray in accordance with the implant planning information, and
a step of generating the implant-placing-guide processing file by using the image of the guide tray in which the guide hole is located.

3. The method for managing production of an implant placing guide according to claim 1,
wherein, when the first planner terminal is possessed by a user who is certified to have only an implant planning qualification,
the method further comprises
after the step d, a step of transmitting a review request signal to one or more preregistered plan reviewing terminals,
a step of transmitting the implant planning information to a first plan reviewing terminal which accepts the review request signal,
a step of receiving a review result of the implant planning information from the first plan reviewing terminal,
a step of re-transmitting the review result to the first planner terminal in response to the review result or transmitting the implant planning information to the dental-clinic terminal, and
a step of executing the step e when approval of the implant planning information is received from the dental-clinic terminal, and
wherein the plan reviewing terminal is possessed by a user who is certified to have a dentist qualification.

4. The method for managing production of an implant placing guide according to claim 3,
wherein a step of transmitting the implant planning information includes a step of transmitting implant planning information to the first plan reviewing terminal, the implant planning information containing a remote access address which is used to share and correct the three-dimensional image with the first planner terminal in real time.

5. The method for managing production of an implant placing guide according to claim 3, further comprising:
a step of remitting a preset planning fee to an account linked to the first planner terminal and remitting a preset plan review fee to an account linked to the first plan reviewing terminal.

6. The method for managing production of an implant placing guide according to claim 1,
wherein the step e includes
a step of transmitting the implant planning information to the dental-clinic terminal, and
a step of generating the implant-placing-guide processing file when approval of the implant planning information is received from the dental-clinic terminal.

7. The method for managing production of an implant placing guide according to claim 1,
wherein the step e includes
a step of transmitting the implant planning information to the dental-clinic terminal,
a step of transmitting a correcting request to the first planner terminal when the correcting request of the implant planning information is received from the dental-clinic terminal,
a step of receiving first implant planning information obtained by reflecting the correcting request from the first planner terminal,
a step of transmitting the first implant planning information to the dental-clinic terminal, and
a step of generating the implant-placing-guide processing file when approval of the implant planning information is received from the dental-clinic terminal.

8. The method for managing production of an implant placing guide according to claim 1,
wherein the implant planning information contains at least one of a size of a fixture, a type of fixture, a fixture placing position, a fixture placing depth, whether or not to perform a bone graft, whether or not to perform a maxillary sinus graft, whether or not to perform a gum graft, and a tool order.

9. The method for managing production of an implant placing guide according to claim 1, further comprising:
a step of requesting a deposit of a preset service charge to the dental-clinic terminal; and
a step of executing the step e or the step f when the service charge is deposited from the dental-clinic terminal.

10. The method for managing production of an implant placing guide according to claim 9, further comprising:
a step of remitting an amount obtained by subtracting a preset fee from the service charge to an account linked to the first planner terminal.

11. The method for managing production of an implant placing guide according to claim 1,
wherein the markers are a radiopaque material.

12. The method for managing production of an implant placing guide according to claim 1,
wherein the markers are disposed at three or more positions.

13. The method for managing production of an implant placing guide according to claim 1,
wherein the implant planning information includes a stereo lithography (STL) type of file.

14. The management method for producing an implant placing guide according to claim 1, further comprising:
step d' of transmitting the implant planning information to the dental-clinic terminal.

15. A non-transitory computer readable medium in which a computer program for executing any one method of the methods according to claims 1 to 14.

16. A method for producing an implant placing guide by a plan reviewing terminal, the method comprising:
a step of receiving a review request signal from a managing server;
a step of receiving from a user an input of whether or not the review request signal is accepted and transmitting to the managing server;
a step of receiving implant planning information generated by a planner terminal from the managing server;
a step of receiving an input of a review result of the implant planning information from the user; and
a step of transmitting the review result to the managing server,
wherein the implant planning information is generated based on a three-dimensional intraoral image acquired by a CT scan in a state where a guide tray filled with an impression material is inserted into an oral cavity of a patient, and wherein the guide tray has one or more markers which are used for matching an image of the guide tray and the three-dimensional image and has an impression of a teeth shape of the patient.

17. The method for producing an implant placing guide by a plan reviewing terminal according to claim 16,
wherein a step of receiving the implant planning information includes a step of receiving implant planning information containing a remote access address which is used to share and correct the three-dimensional image with the planner terminal in real time.

18. A non-transitory computer readable medium in which a computer program for executing any one method of the methods according to claims 16 and 17.

* * * * *